United States Patent [19]

Joseph

[11] Patent Number: 4,765,981

[45] Date of Patent: Aug. 23, 1988

[54] TREATMENT OF GASTROINTESTINAL DISORDERS

[76] Inventor: Anna M. Joseph, 618 Bellwood Rd., Newport News, Va. 23605

[21] Appl. No.: 660,966

[22] Filed: Oct. 15, 1984

[51] Int. Cl.$^4$ ............................................. A61K 35/78
[52] U.S. Cl. ................................ 424/195.1; 514/867; 514/872; 426/436
[58] Field of Search ..................... 424/195.1; 514/867, 514/872; 426/436

[56] References Cited

U.S. PATENT DOCUMENTS

| | | | |
|---|---|---|---|
| 1,414,576 | 5/1922 | Mock | 426/655 |
| 3,767,784 | 10/1973 | Gluck | 424/28 |
| 4,028,468 | 6/1977 | Hohner et al. | 426/436 |

OTHER PUBLICATIONS

American Dispensatory, pp. 152-153, 1870.
Chem. Abstrs. 61: 7440a, 1964.
Hirschhorn, The Home Herbal Doctor, p. 88, 1982.
"McGraw-Hill Encyclopedia of Science and Technology", vol. 11, p. 40, 1977.
H. Moore, "On Uncle Sam's Water Wagon", p. 170, 1919.

*Primary Examiner*—John W. Rollins, Jr.
*Attorney, Agent, or Firm*—George F. Helfrich

[57] ABSTRACT

Gastrointestinal disorders, especially those in the very young and the very old which are manifested by nausea, vomiting, diarrhea, increased flatus, cramping, and the like, are treated by the oral administration to the patient of a therapeutically-effective amount of an aqueous extract of oatmeal. This extract is especially effective in the treatment of infant colic and infant intolerance of milk and synthetic formulas.

2 Claims, No Drawings

TREATMENT OF GASTROINTESTINAL DISORDERS

BACKGROUND OF THE INVENTION

1. Field of the Invention

The present invention relates to methods of treating illnesses in humans. It relates particularly to a method of treating human patients having gastrointestinal disorders manifested by nausea, vomiting, diarrhea, increased flatus, cramping, and the like, especially in the very young and the very old. The present invention is especially suitable in the treatment of infant colic and infant intolerance of milk and synthetic formulas.

2. Prior Art

Over the years a very large number of methods have been proposed for the treatment of gastrointestinal disorders in humans, certain of which have been proven to be highly efficacious. However, in the very young and the very old, significant difficulties still persist in the treament of gastrointestinal disorders characterized by nausea, vomiting, diarrhea, increased flatus, cramping, and the like. As a primary example, infant colic is especially troublesome. Infant colic refers to an attack of abdominal discomfort caused by spasmodic contractions of the intestine, most common during the first three months of life. The infant may pull up his arms and legs, cry loudly, turn red-faced, and expell gas from the intestine or belch it up from the stomach. In severely aggravated cases, vomiting and diarrhea accompany the other symptoms. Also extremely troublesome in infants is the physical intolerance—oftentimes allergic in nature—of milk, including mother's milk, and the various milk substitutes available in the form of snythetic baby formulas. In addition to nausea, vomiting, increased flatus, and cramping, this condition sometimes results in bleeding from the rectum and severe skin eruptions.

In addition to picking up the colicky infant, "bubbling" it, and soothing it with tender, loving care, parents find it often necessary to substitute some preparation for the milk or formula which the infant is ingesting. Similarly, the intolerant or allergic infant must find a substitute for the offending milk or formula, as the most successful means of preventing the symptoms of intolerance or allergy is avoidance of the offending allergen. In both cases, however, it is difficult to find a substitute which is not only non-offending, but also sufficiently nutritious. This is self-evident in the caring for the very young, e.g., the infant and premature infant, who are unable to ingest solid food. However, it is also often encountered in the caring for the very old and infirm, who, for a wide variety of reasons do not take solid foods well.

In the caring for infants over the years, mother's milk and cow's milk have given way first to goat's milk and donkey's milk, and then to condensed milk and evaporated milk. In fact, many children of the 30's and 40's were brought up on a formula of evaporated milk, corn syrup, and water. Although most of these children managed to develop more or less adequately on such a preparation, it was found by the medical profession to have numerous therapeutic and nutritional drawbacks. As a result, the various baby "formulas" came into being.

All baby formulas employed today have either a heat-treated cow's milk base or a soy isolate base. The heat treatment attenuates the protein content in an attempt to meet various needs of various infants. However, there are still a number of infants who are unable to tolerate milk of any kind, as well as any of the formulas available today. The method of the present invention provides a tolerable, nutritional alternative for a number of patients.

The closest art known to the applicant is set forth below:

U.S. Pat. No. 1,414,576 discloses a method of preparing an improved food product. The method comprises mixing rolled oats or oatmeal with boiling water and cooking this mixture for 4–6 hours. The liquid from this mixture is first separated from the solid residue and then concentrated by heating. Final reduction of this solution to dryness is effected in a vacuum. The resulting dried product is ground and packaged for consumption as an improved food product. However, there is no disclosure or suggestion in this reference that the intermediate extract could be used for any kind of therapeutic purpose.

U.S. Pat. No. 312,869 discloses a process for producing extracts from cereal grains, which process comprises soaking the grain to soften and remove the bran coating, removing this bran coating in flakes, then boiling the bran to produce an extract, straining the solid from the liquid extract, followed by concentrating the liquid extract for use in baker's and confectioner's articles, soups and the like. However, there is no disclosure or suggestion in this reference that the concentrated extract could be used for any therapeutic purpose.

U.S. Pat. No. 4,028,468 discloses a process wherein oat groats are ground to form a coarse branny fraction and a fine fraction. The coarse fraction is separated and formed into an aqueous slurry, which is subjected to an extracton and separation process to isolate oat gum and and oat protein, together with other by-products. However, there is no disclosure or mention whatever that any aqueous extract prepared in this process could be used for any therapeutic purpose.

SUMMARY OF THE PRESENT INVENTION

It is the primary object of the present invention to provide what the prior art does not provide, viz. a very simple, yet highly efficacious process for treating patients having gastrointestinal disorders, especially those in the very young and the very old which are manifested by nausea, vomiting, diarrhea, increased flatus, cramping, and the like. This object is achieved, and the inadequacies of the prior art are supplied by the oral administration to the patient of a therapeutically-effective amount of an aqueous extract of oatmeal. This extract is advantageously prepared by mixing oatmeal or rolled oats with water to form a slurry, bringing the slurry to a boil, followed by separating the aqueous extract from the solid oatmeal, and cooling the separated aqueous extract to room temperature. Very beneficial results are obtained if the slurry is maintained at the boil for at least one hour prior to separation of the aqueous extract from the solid oatmeal. The very best results are obtained when the oatmeal employed consists of rolled oats having the following analysis for each ounce thereof: calories—110; protein—5 g.; carbohydrate—18 g.; fat—2 g.; cholesterol—nil; sodium—10 mg.; potassium—55 mg.; and trace quantities of Vitamins A, C, D, thiamine, niacin, riboflavin, calcium, iron, and phosphorous. This aqueous extract is best administered orally in amounts of 4 to 8 fluid ounces every 4 hours until the symptoms of the gastrointestinal disorder subside.

DETAILED DESCRIPTION OF THE PREFERRED EMBODIMENTS

Following is an example illustrating the best mode comprehended by the inventor for the practice of the present invention.

EXAMPLE

Two cups of oatmeal was added to 10 cups of water in a saucepan. The slurry so formed was brought to a boil with stirring and allowed to simmer for 3 hours. The aqueous extract was then separated by straining from the solid oatmeal and cooled to room temperature.

Although oatmeal from various sources has been found to have utility in the practice of the present invention, the very best results are obtained when the oatmeal employed is rolled oats having the following analysis for each ounce thereof: calories—110; protein—5 g.; carbohydrate—18 g.; fat—2 g.; cholesterol—nil; sodium—10 mg.; potassium—55 mg.; and trace quantities of Vitamins A, C, D, thiamine, niacin, riboflavin, calcium, iron, and phosphorous. This oatmeal is marketed under the brand name "QUAKER OLD FASHIONED" oats by the Quaker Oats Company, Chicago, Ill.

Although the thickness of the slurry employed in this example affords excellent handling, a thicker or thinner consistency may be employed without any reduction in the therapeutic value of the resulting extract.

After the slurry has been brought to a boil, it is advantageously maintained at or near thereto, as by simmering, for at least 1 hour, and most advantageously, for at least 3 hours prior to separation of the aqueous extract from the solid oatmeal. Separation is accomplished by standard means such as filtration or straining through a fine mesh screen.

After the aqueous extract was separated from the solid oatmeal and cooled to room temperature, it was employed without more in the treatment of patients having gastrointestinal disorders. However, if desired, a small amount of sugar may be added, in order to make the liquid more desirable, especially for the young.

The aqueous extract according to the present invention was administered orally to two children suffering from severe gastrointestinal disorders. Both were but weeks old, one having been a full term baby, the other, 2 months premature. Both had severe vomiting, diarrhea, increased flatus, and cramping, in addition to rectal bleeding and severe skin eruptions. Neither could tolerate mother's milk, cow's milk, or any available synthetic formula. The aqueous extract of the present invention was administered orally (by means of an infant bottle) in amounts of 4 to 8 fluid ounces every 4 hours. Severe symptoms began to subside after about 36 hours. After about one week the symptoms had completely disappeared.

The aqueous extract of the present invention was administered in the same manner and with equally beneficial results to infants having colic, and infants having an allergic intolerance of milk and synthetic formulas based on soy isolates. It was also administered orally to the infirm who were suffering from nausea, vomiting, diarrhea, increased flatus and severe cramping. The same excellent results were achieved.

The present invention has been described in detail with respect to certain preferred embodiments. Variations in this detail may be effected without any departure from the spirit and scope of the invention, as described in the following claims.

I claim:

1. A process for treating patients having a gastrointestinal disorder selected from the group consisting of infant colic, infant intolerance of milk and synthetic formulas, and intolerance of solid foods by the elderly or the infirm, the gastrointestinal disorder manifested by one of nausea, vomiting, diarrhea, increased flatus, and cramping, which process comprises orally administering to the patient an amount effective to bring about the removal of alleviation of the gastrointestinal disorder of an aqueous extract resulting from boiling a slurry of water and raw oatmeal and separating the aqueous phase from the solid oatmeal.

2. The process of claim 1, wherein the aqueous extract of oatmeal is orally administerd in amounts of 4 to 8 fluid ounces every 4 hours until the symptoms of the gastrointestinal disorder subside.

* * * * *